United States Patent [19]

Matsumoto et al.

[11] Patent Number: 4,535,089
[45] Date of Patent: Aug. 13, 1985

[54] ALKYLOXAZOLYLACETIC ACID DERIVATIVE FOR THE TREATMENT OF HYPERLIPIDEMIA

[75] Inventors: Kazuo Matsumoto, Ibaraki; Seiichi Takabe, Amagasaki; Kohki Takashima, Tokyo, all of Japan

[73] Assignee: Tanabe Seiyaku Co., Ltd., Osaka, Japan

[21] Appl. No.: 494,023

[22] Filed: May 12, 1983

[30] Foreign Application Priority Data

May 19, 1982 [JP] Japan .................................. 57-85282

[51] Int. Cl.³ .............................................. A61K 31/42
[52] U.S. Cl. ..................................... 514/374; 548/235
[58] Field of Search ......................... 548/235; 424/272

[56] References Cited

U.S. PATENT DOCUMENTS 3,470,195 9/1969 O'Mant .............................. 548/235

Primary Examiner—Donald G. Daus
Assistant Examiner—S. A. Gibson
Attorney, Agent, or Firm—Birch, Stewart, Kolasch & Birch

[57] ABSTRACT

A alkyloxazolylacetic acid derivative of the formula:

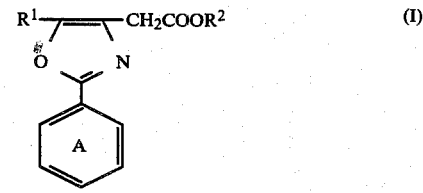

wherein Ring A is phenyl or halogenophenyl, $R^1$ is lower alkyl of one to 5 carbon atoms and $R^2$ is hydrogen or lower alkyl of one to 3 carbon atoms. The compound (I) is useful as a hypolipidemic agent.

3 Claims, No Drawings

ALKYLOXAZOLYLACETIC ACID DERIVATIVE FOR THE TREATMENT OF HYPERLIPIDEMIA

This invention relates to a novel alkyloxazolylacetic acid derivative and processes for preparing same. More particularly, it relates to an alkyloxazolylacetic acid derivative of the formula:

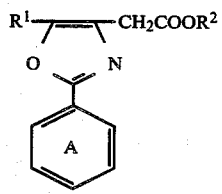

wherein Ring A is phenyl or halogenophenyl, $R^1$ is lower alkyl of one to 5 carbon atoms and $R^2$ is hydrogen or lower alkyl of one to 3 carbon atoms.

The compound (I) in which $R^2$ is hydrogen can exist in the form of either a free acid or a pharmaceutically acceptable salt thereof, and the present invention also includes within its scope such pharmaceutically acceptable salts of the compound (I).

Hyperlipidemia is known to be one of the important causative factors of arteriosclerosis, and various compounds such as dextran sulfate, simfibrate (chemical name: 2-(4-chlorophenoxy)-2-methylpropanoic acid 1,3-propanediyl ester), nicomol (chemical name: nicotinic acid 1,1,3,3-tetraester with 2-hydroxy-1,1,3,3-cyclohexanetetramethanol), clofibrate (chemical name: 2-(4-chlorophenoxy)-2-methylpropanoic acid ethyl ester) and vitamin E nicotinate have been used for the treatment or prophylaxis of said hyperlipidemia.

As a result of investigations, it has now been found that the alkyloxazolylacetic acid derivative (I) of the present invention is useful as a hypolipidemic agent. In particular, the alkyloxazolylacetic acid derivative (I) shows potent hypolipidemic activity without undesirable side effects such as hepatic disfunction. Further, the alkyloxazolylacetic acid derivative (I) also shows a potent platelet aggregation-inhibiting activity.

Representative examples of the alkyloxazolylacetic acid derivative include those of the formula (I) in which Ring A is phenyl or halogenophenyl such as fluorophenyl, chlorophenyl, bromophenyl and iodophenyl, $R^1$ is lower alkyl of one to 5 carbon atoms such as methyl, ethyl, n-propyl, isopropyl, n-butyl, isobutyl, n-pentyl and isopentyl; and $R^2$ is hydrogen or lower alkyl of one to 3 carbon atoms such as methyl, ethyl and propyl. Among them, a preferred subgenus is the compound of the formula (I) in which Ring A is phenyl, 4-fluorophenyl or 4-chlorophenyl; $R^1$ is methyl, isopropyl, isobutyl or n-pentyl; and $R^2$ is hydrogen or ethyl. A more preferred subgenus is the compound of the formula (I) in which Ring A is 4-chlorophenyl or 4-fluorophenyl; $R^1$ is metnyl, isopropyl or n-pentyl; and $R^2$ is hydrogen or ethyl. A further preferred subgenus is the compound of the formula (I) in which Ring A is 4-chlorophenyl or 4-fluorophenyl; $R^1$ is isopropyl; and $R^2$ is hydrogen or ethyl.

According to the present invention, the compound (I) in which $R^2$ is lower alkyl of one to 5 carbon atoms is prepared by subjecting a 3-benzoylaminopropionate derivative of the formula:

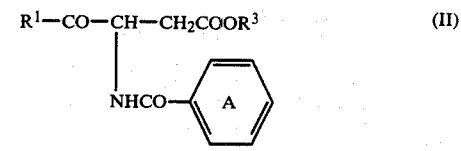

wherein $R^3$ is lower alkyl of one to 5 carbon atoms, and Ring A and $R^1$ are the same as defined above, to dehydrative cyclization to give an alkyloxazolylacetate derivative of the formula:

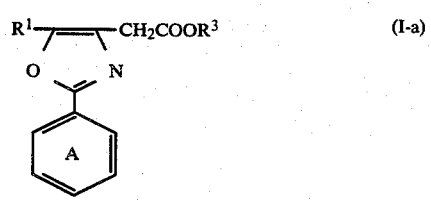

wherein Ring A, $R^1$ and $R^3$ are the same as defined above.

On the other hand, compound (I) in which $R^2$ is hydrogen is prepared by hydrolyzing the compound (I-a) to give an alkyloxazolylacetic acid derivative of the formula:

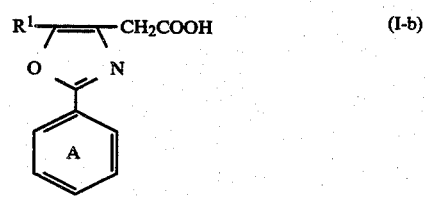

wherein Ring A and $R^1$ are the same as defined above.

The dehydrative cyclization of the compound (II) is accomplished in a solvent in the presence of a dehydrating agent. The dehydrating agent includes, for example, phosphorus oxychloride, phosphorus trichloride, phosphorus pentachloride, thionyl chloride, oxalyl chloride, phosgene and phosphorus pentoxide. p-Toluenesulfonic acid and sulfuric acid are also used in a catalytic amount as the dehydrating agent. Chloroform, methylene chloride, carbon tetrachloride, benzene, toluene, xylene, tetrahydrofuran and dimethylformamide are suitable as the solvent. It is preferred to carry out the reaction at a temperature of −5° C. to 130° C., especially at a temperature of −5° to 60° C.

The hydrolysis of the compound (I-a) is accomplished by contacting said compound with an acid or an alkali agent in a solvent. The acid includes, for example, mineral acids such as hydrochloric acid or sulfuric acid. On the other hand, the alkali agent includes, for example, alkali metal hydroxides such as sodium hydroxide or potassium hydroxide. Water, alkanol (e.g., methanol, ethanol, propanol), tetrahydrofuran, dioxane and a mixtures thereof are suitable as the solvent. It is preferred to carry out the reaction at a temperature of 0° to 100° C., especially 10° to 30° C.

In view of the potent hypolipidemic activity of the compound (I) obtained above, said compound of the present invention is useful for the therapeutic treatment or prophylaxis of various hyperlipidemias such as hypercholesterolemia, hypertriglyceridemia, hyperlipemia and the like. Moreover, the compound (I) of the present invention shows less hepatomegaly or other hepatic disorders as compared with clofibrate, and is particularly suitable for treatment of the above-mentioned diseases without such undesirable side effects. Further, the compound (I) of the present invention has a potent platelet aggregation-inhibiting activity which is desirable for the hypolipidemic agent.

The compound (I) ($R^2$=H) of the present invention can be used for pharmaceutical use in the form of either a free acid or a pharmaceutically acceptable salt thereof. Pharmaceutically acceptable salts of the compound (I) ($R^2$=H) include, for example, alkali metal salts such as sodium and potassium salts; alkaline earth metal salts such as calcium and magnesium salts; salts thereof with amino acids such as lysine, ornithine, arginine and histidine salts; and ammonium salt. Such pharmaceutically acceptable salts may be prepared, for example, by neutralizing the free acid with a stoichiometrically equimolar amount of a base such as an alkali metal hydroxide, an alkaline earth metal hydroxide, ammonia or a basic amino acid. The compound (I) and a salt thereof can be administered either orally or parenterally. For oral administration, the compound (I) or a salt thereof may be used in the form of tablets, powder, capsules, granules and the like. Known medicinal excipients such as calcium carbonate, calcium phosphate, corn starch, potato starch, sugar, lactose, talc, magnesium stearate and so forth may be used in making these pharmaceutical preparations. Alternatively, the compound (I) or a salt thereof may be used for oral administration in the form of aqueous or oily suspensions, solutions, syrps or elixirs. On the other hand, injections and suppositories are suitable for parenteral administration of the compound (I) or its salts, and said injections may be made in the form of solutions or suspensions, if required, in conjunction or admixture with distilled water, essential oil (e.g., peanut oil, corn oil) or non-aqueous solvent (e.g., polyethyleneglycol, polypropyleneglycol, lanoline, coconut oil). The daily dose of the compound (I) or a salt thereof may vary depending on the administration route, the age, weight or conditions of patients, and the severity of diseases to be treated. In general, however, a preferred daily dose of said compound (I) or a salt thereof may be 1 to 20 mg, especially 5 to 15 mg, per kilogram of body weight per day. Besides, the compound (I) of the present invention has low toxicity and hence has high safety for use in the therapeutic treatment or prophylaxis of hyperlipidemia. For instance, when ethyl 2-[2-(4-chlorophenyl)-5-methyl-4-oxazolyl]acetate or ethyl 2-[2-(4-chlorophenyl)-5-n-pentyl-4-oxazolyl]acetate is administered orally to mice at the dose of 1000 mg/kg, no mouse dies during the period of 7 days after administration.

Concomitantly, the starting compound (II) of the present invention is a novel compound and can be prepared, for example, according to the method shown in the following reaction scheme:

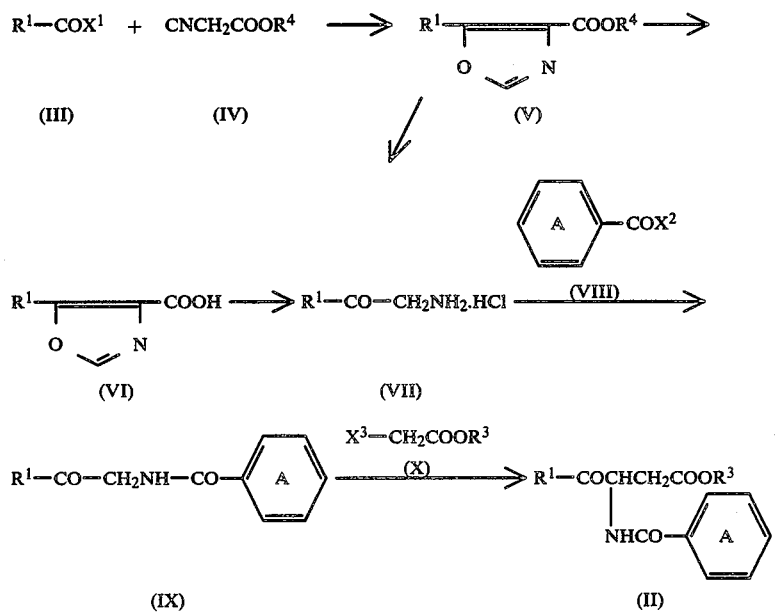

wherein $R^4$ is lower alkyl, $X^1$ is halogen or a group of the formula: $R^1$—COO—, $X^2$ and $X^3$ are halogen, and Ring A, $R^1$ and $R^3$ are the same a defined above.

The reaction of the aliphatic carboxylic acid derivative (III) with the isocyanoacetate compound (IV) is carried out in a solvent (e.g., tetrahydrofuran, dioxane, dimethylformamide) in the presence of a base such as sodium methoxide, potasium t-butoxide or 1,8-diazabicyclo(5.4.0)undecene-7 at −50° to 50° C. The oxazole derivative (V) thus obtained is saponified with an alkali metal hydroxide (e.g., sodium hydroxide, potassium hydroxide) at 20° to 50° C., and the reaction mixture is acidified to give the oxazolecarboxylic acid derivative (VI) which is then treated with a mineral acid (e.g., 2N hydrochloric acid-methanol) at 40° to 80° C. to give the aminoketone compound (VII). Alternatively, the aminoketone compound (VII) may be prepared by hydrolyzing the compound (V) with a mineral acid, for example, by treating the compound (V) with 4N hydrochloric acid at 50° to 80° C. The subsequent reaction of the aminoketone compound (VII) with the benzoyl halide (VIII) is carried out in a solvent (e.g., ethyl acetate, benzene) in the presence of an acid acceptor (e.g., sodium hydroxide, sodium bicarbonate) at −20° to 20° C. The N-benzoylamine derivative (IX) thus obtained is then reacted with the halogenoacetate compound (X) in a solvent (e.g., tetrahydrofuran, dioxane, dimethylformamide, dimethylsulfoxide, acetonitrile) in the presence of an acid acceptor (e.g., potassium hydroxide, sodium ethoxide, potassium t-butoxide, sodium hydride) at −50° to 30° C. to give the 3-benzoylaminopropionate derivative (II).

Practical and presently-preferred embodiments of the present invention are illustratively shown in the following lines.

EXPERIMENT 1

Hypolipidemic activity

A test compound (50 mg %) was added to a commercial diet, and male SD rats (body weight: 120–140 g, a group of 5 rats) were fed with the diet ad libitum for one week. After the experimental period, blood was collected from the tail vein of the rats under ether anesthesia. Then, liver was excised from the rats and the weight thereof was measured. On the other hand, serum cholesterol and serum triglyceride were measured according to the methods of Zak (Amer. J. Clin. Pathol., Vol. 24, page 1307(1954)) and Van Handel-Zilversmit (J. Lab. & Clin. Med., Vol. 50, page 152(1957)), respectively. Based on the results obtained above, the decrease (%) in serum cholesterol or triglyceride and increase (%) in liver weight were calculated by the following formulae:

$$\text{Decrease (\%) in serum cholesterol or triglyceride} = \left[1 - \frac{\text{Serum cholesterol or triglyceride (mg/ml) in the medicated group}}{\text{Serum cholesterol or triglyceride (mg/ml) in the control group}}\right] \times 100$$

$$\text{Increase (\%) in liver weight} = \left[\frac{\text{Liver weight in the medicated group}}{\text{Liver weight in the control group}} - 1\right] \times 100$$

(Results)

The results are shown in the following Table 1. Concomitantly, each of the test compounds of the present invention showed no substantial increase in liver weight, whereas clofibrate showed 12% increase in liver weight.

TABLE 1

| Test compounds | Decrease (%) in serum cholesterol | Decrease (%) in serum triglyceride |
|---|---|---|
| (The compounds of the present invention) | | |
| 2-[2-(4-chlorophenyl)-5-methyl-4-oxazolyl]acetic acid | 14 | 48 |
| Ethyl 2-[2-(4-chlorophenyl)-5-methyl-4-oxazolyl]acetate | 19 | 36 |
| 2-[2-(4-chlorophenyl)-5-isopropyl-4-oxazolyl]-acetic acid | 12 | 39 |
| Ethyl 2-[2-(4-chlorophenyl)-5-isopropyl-4-oxazolyl]acetate | 18 | 55 |
| 2-[2-(4-chlorophenyl)-5-pentyl-4-oxazolyl]acetic acid | 19 | 60 |
| Ethyl 2-[2-(4-chloro- | 15 | 52 |

TABLE 1-continued

| Test compounds | Decrease (%) in serum cholesterol | Decrease (%) in serum triglyceride |
|---|---|---|
| phenyl)-5-pentyl-4-oxazolyl]acetate | | |
| 2-[2-(4-fluorophenyl)-5-isopropyl-4-oxazolyl]-acetic acid | 21 | 42 |
| Ethyl 2-[2-(4-fluorophenyl)-5-isopropyl-4-oxazolyl]acetate | 23 | 33 |
| 2-[2-(4-fluorophenyl)-5-isobutyl-4-oxazolyl-acetic acid | 11 | 51 |
| Ethyl 2-[2-(4-fluorophenyl)-5-isobutyl-4-oxazolyl]acetate | 13 | 66 |
| (Positive control) | | |
| Clofibrate | 15 | 16 |

EXPERIMENT 2

Platelet aggregation-inhibiting activity

Blood was collected from the abdominal aorta of male SD rats (body weight: 250–300 g) which were anesthetized with ether. Nine volumes of said blood were mixed with one volume of an aqueous 3.8% (w/v) trisodium citrate solution, and the mixture was centrifuged at 500×g for 5 minutes to give platelet-rich plasma (hereinafter referred to as "PRP") as the supernatant solution. The bottom layer was further centrifuged at 1000×g for 10 minutes to give platelet-poor plasma (hereinafter referred to as "PPP") as the supernatant solution. PRP was diluted with PPP so that the blood platelet count was 8–10×$10^5$ cells/mm³. Then, a mixture of 200 μl of said diluted PRP and 25 μl of a test compound solution (final concentration: 100 μg/ml) was introduced into a glass cell of SIENCO aggregometer (Sienco Inc., Morrison, Colo. Model DP-247-D). After the mixture was stirred at 1100 rpm at 37° C. for 2 minutes, 25 μl of a collagen solution (prepared by Holmsen's method described in Biochim. Biophys. Acta, Vol. 186, page 254(1969)) was added thereto, and the percentage inhibition of platelet aggregation was calculated in accordance with the following formula from the degree of the platelet aggregation which was estimated by Born's method (Nature, 194, page 927(1962)).

$$\text{Percentage inhibition of platelet aggregation} = \left[1 - \frac{\text{Degree of platelet aggregation which was estimated by adding test compound}}{\text{Degree of platelet aggregation which was estimated without adding test compound}}\right] \times 100$$

Further, on the basis of said percentage inhibition calculated above, the platelet aggregation-inhibiting activity of the test compound was expressed as (−) if the test compound showed less than 10% inhibition of platelet aggregation; or (+) if the test compound showed not less than 10% inhibition of platelet aggregation.

Results

The results are shown in the following Table 2.

TABLE 2

| Test compounds | Platelet aggregation-inhibiting activity |
| --- | --- |
| (The compounds of the present invention) | |
| 2-[2-(4-chlorophenyl)-5-isopropyl-4-oxazolyl]acetic acid | + |
| Ethyl 2-[2-(4-chlorophenyl)-5-isopropyl-4-oxazolyl]acetate | + |
| Ethyl 2-[2-(4-fluorophenyl)-5-isopropyl-4-oxazolyl]acetate | + |
| Ethyl 2-[2-(4-fluorophenyl)-5-isobutyl-4-oxazolyl]acetate | + |
| Ethyl 2-[2-(4-chlorophenyl)-5-isobutyl-4-oxazolyl]acetate | + |
| 2-[2-(4-fluorophenyl)-5-isopropyl-4-oxazolyl]acetic acid | + |
| 2-(2-phenyl-5-isopropyl-4-oxazolyl)acetic acid | + |
| (Positive control) | |
| Clofibrate | − |

EXPERIMENT 3

Platelet aggregation-inhibiting activity

A test compound was suspended in a solution containing 0.25% of carboxymethylcellulose (sodium salt) and 0.01% of Tween 80, and the suspension was administered orally to make SD rats (a group of 4 rats). One hour after administration of the test compound (dose: 100 mg/kg), blood was collected from the abdominal aorta of the rats under ether anesthesia. Thereafter, said blood was treated in the same manner as described in Experiment 2, and the percentage inhibition of platelet aggregation was calculated in accordance with the following formula:

$$\text{Percentage inhibition of platelet aggregation} = \left[1 - \frac{\text{Degree of platelet aggregation in the medicated group}}{\text{Degree of platelet aggregation in the control group}}\right] \times 100$$

Results

The results are shown in the following Table 3.

TABLE 3

| Test compounds | Percentage inhibition of platelet aggregation (%) |
| --- | --- |
| (The compound of the present invention) | |
| 2-(2-phenyl-5-isopropyl-4-oxazolyl)acetic acid | 97 ± 2 |
| (Control) | |
| Clofibrate | 53 ± 19 |

PREPARATION OF FINAL PRODUCT COMPOUNDS

EXAMPLE 1

10 g of ethyl 3-(4-chlorobenzolylamino)-3-isobutyrylpropionate are dissolved in 30 ml of dimethylformamide and 7.1 g of phosphorus oxychloride are added dropwise thereto at 0° C. to 5° C. The mixture is stirred at the same temperature for 3 hours, and further stirred at room temperature for 2 hours. After the reaction, the mixture is poured into water, and the aqueous mixture is neutralized with sodium bicarbonate and then extracted with ethyl acetate. The extract is washed with water, dried and then condensed under reduced pressure to remove solvent. The residue is recrystallized from ethanol, whereby 7.5 g of ethyl 2-[2-(4-chlorophenyl)-5-isopropyl-4-oxazolyl]acetate are obtained. Yield: 79.4%.

M.p. 70°–71° C.

IR $\nu_{max}^{Nujol}$ (cm$^{-1}$): 1725.

EXAMPLE 2

6.5 g of ethyl 3-benzoylamino-3-isobutyrylpropionate, 30 ml of dimethylformamide and 4.8 g of phosphorus oxychloride are treated in the same manner as described in Example 1. 5.0 g of ethyl 2-(2-phenyl-5-isopropyl-4-oxazoly)acetate are thereby obtained. Yield: 81.4%.

M.p. 37°–38° C.

IR $\nu_{max}^{Nujol}$ (cm$^{-1}$): 1730.

EXAMPLE 3

7.0 g of ethyl 3-(4-fluorobenzoylamino)-3-isobutyrylpropionate, 35 ml of dimethylformamide and 5.7 g of phosphorus oxychloride are treated in the same manner as described in Example 1. 4.0 g of ethyl 2-[2-(4-fluorophenyl)-5-isopropyl-4-oxazolyl]acetate are thereby obtained. Yield: 60.6%.

M.p. 59°–60° C.

IR $\nu_{max}^{Nujol}$ (cm$^{-1}$): 1725.

EXAMPLE 4

2.5 g of ethyl 3-(4-chlorobenzoylamino)-3-isovalerylpropionate, 10 ml of dimethylformamide and 2.3 g of phosphorus oxychloride are treated in the same manner as described in Example 1. 1.5 g of ethyl 2-[2-(4-chlorophenyl)-5-isobutyl-4-oxazolyl]acetate are thereby obtained. Yield: 63.3%.

M.p. 56°–57° C.

IR $\nu_{max}^{Nujol}$ (cm$^{-1}$): 1730, 1645.

EXAMPLE 5

3.5 g of ethyl 3-(4-fluorobenzoylamino)-3-isovalerylpropionate, 20 ml of dimethylformamide and 4.1 g of phosphorus oxychloride are treated in the same manner as described in Example 1. 2.5 g of ethyl 2-[2-(4-fluorophenyl)-5-isobutyl-4-oxazolyl]acetate are thereby obtained. Yield: 75.5%.

M.p. 60°–61° C.

IR $\nu_{max}^{Nujol}$ (cm$^{-1}$): 1730, 1643.

EXAMPLE 6

2.98 g of ethyl 3-(4-chlorobenzoylamino)-3-acetylpropionate, 15 ml of dimethylformamide and 1.8 g of phosphorus oxychloride are treated in the same manner as described in Example 1. 1.98 g of ethyl 2-[2-(4-chlorophenyl)-5-methyl-4-oxazolyl]acetate are thereby obtained. Yield: 70.9%.

M.p. 69°–70° C.
IR $\nu_{max}^{Nujol}$ (cm$^{-1}$): 1725, 1645.

EXAMPLE 7

2.0 g of ethyl 3-(4-chlorobenzoylamino)-3-caproyl-propionate, 10 ml of dimethylformamide and 1.0 g of phosphorus oxychloride are treated in the same manner as described in Example 1. 1.6 g of ethyl 2-[2-(4-chlorophenyl)-5-n-pentyl-4-oxazolyl]acetate are thereby obtained. Yield: 84.2%.
M.p. 52°–53° C.
IR $\nu_{max}^{Nujol}$ (cm$^{-1}$): 1725, 1645.

EXAMPLE 8

6 g of ethyl 2-[2-(4-chlorophenyl)-5-isopropyl-4-oxazolyl]acetate are dissolved in a mixture of 100 ml of methanol and 10 ml of water, and 4.4 g of potassium hydroxide are added thereto. The mixture is stirred at room temperature for 10 hours. After the reaction, the mixture is condensed under reduced pressure to remove methanol. Water is added to the residue, and the aqueous mixture is adjusted to pH 2 with conc. hydrochloric acid, and then extracted with ethyl acetate. The extract is washed with water, dried and then evaporated under reduced pressure to remove solvent. The residue is recrystallized from ethanol, whereby 5 g of 2-[2-(4-chlorophenyl)-5-isopropyl-4-oxazolyl]acetic acid are obtained. Yield: 91.7%.
M.p. 171°–172° C.
IR $\nu_{max}^{Nujol}$ (cm$^{-1}$): 1720.

EXAMPLE 9

2.73 g of ethyl 2-(2-phenyl-5-isopropyl-4-oxazolyl)acetate, 20 ml of methanol, 5 ml of water and 1.1 g of potassium hydroxide are treated in the same manner as described in Example 8. 2.39 g of 2-(2-phenyl-5-isopropyl-4-oxazolyl)acetic acid are thereby obtained. Yield: 97.4%.
M.p. 141°–143° C.
IR $\nu_{max}^{Nujol}$ (cm$^{-1}$): 1725.

EXAMPLE 10

2.0 g of ethyl 2-[2-(4-fluorophenyl)-5-isopropyl-4-oxazolyl]acetate, 15 ml of methanol, 5 ml of water and 0.8 g of potassium hydroxide are treated in the same manner as described in Example 8. 1.5 g of 2-[2-(4-fluorophenyl)-5-isopropyl-4-oxazolyl]acetic acid are thereby obtained. Yield: 83.3%.
M.p. 137°–138° C.
IR $\nu_{max}^{Nujol}$ (cm$^{-1}$): 1725.

EXAMPLE 11

1.53 g of ethyl 2-[2-(4-fluorophenyl)-5-isobutyl-4-oxazolyl]acetate, 10 ml of methanol, 3 ml of water and 0.6 g of potassium hydroxide are treated in the same manner as described in Example 8. 1.37 g of 2-[2-(4-fluorophenyl)-5-isobutyl-4-oxazolyl]acetic acid are thereby obtained. Yield: 98.9%.
M.p. 125°–126° C.
IR $\nu_{max}^{Nujol}$ (cm$^{-1}$): 1719.

EXAMPLE 12

2.0 g of ethyl 2-[2-(4-chlorophenyl)-5-methyl-4-oxazolyl]acetate, 15 ml of methanol, 5 ml of water and 0.8 g of potassium hydroxide are treated in the same manner as described in Example 8. 1.50 g of 2-[2-(4-chlorophenyl)-5-methyl-4-oxazolyl]acetic acid are thereby obtained. Yield: 83.3%.
M.p. 160°–161° C.
IR $\nu_{max}^{Nujol}$ (cm$^{-1}$): 1695.

EXAMPLE 13

1.0 g of ethyl 2-[2-(4-chlorophenyl)-5-n-pentyl-4-oxazolyl]acetate, 10 ml of methanol, 3 ml of water and 0.4 g of potassium hydroxide are treated in the same manner as described in Example 8. 0.8 g of 2-[2-(4-chlorophenyl)-5-n-pentyl-4-oxazolyl]acetic acid are thereby obtained. Yield: 87.2%.
M.p. 136°–137° C.
IR $\nu_{max}^{Nujol}$ (cm$^{-1}$): 1705.

PREPARATION OF STARTING COMPOUNDS

Preparation 1

(1) 13.7 g of sodium methoxide are dissolved in 200 ml of dimethylformamide, and 19.4 g of methyl α-isocyanoacetate are added dropwise thereto at −50° C. to −40° C. The mixture is stirred at the same temperature for 30 minutes. 25 g of isobutyryl chloride are gradually added to the mixture at −50° C. to −40° C., and said mixture is stirred at the same temperature for 2 hours. After the reaction, the mixture is adjusted to pH 3–4 with acetic acid and then condensed under reduced pressure to remove solvent. The residue is extracted with ethyl acetate and the extract is washed with aqueous sodium bicarbonate solution and water, successively. The extract is then dried and condensed under reduced pressure to remove solvent. 23.1 g of 5-isopropyl-4-methoxycarbonyloxazole are obtained. Yield: 70.0%.
M.p. 49°–50° C.
IR $\nu_{max}^{Nujol}$ (cm$^{-1}$): 3140, 3090, 1700, 1660, 1615.

(2) 23.1 g of 5-isopropyl-4-methoxycarbonyloxazole are dissolved in a mixture of 200 ml of methanol and 200 ml of water, and 15.3 g of potassium hydroxide are added thereto. The mixture is stirred at room temperature over night, and condensed under reduced pressure to remove methanol. The residue is dissolved in water and the aqueous solution is adjusted to pH 2–3 with conc. hydrochloric acid. Said solution is extracted with ethyl acetate, and the extract is washed with water, dried and then evaporated to remove solvent. 18 g of 5-isopropyl-4-oxazolecarboxylic acid are obtained. Yield: 85.3%.
M.p. 136°–137° C.
IR $\nu_{max}^{Nujol}$ (cm$^{-1}$): 3120, 1700, 1635.

(3) A mixture of 13 g of 5-isopropyl-4-oxazolecarboxylic acid and 60 ml of 4N-hydrochloric acid is refluxed for 4 hours. After the reaction, the mixture is condensed under reduced pressure and acetone is added to the residue. The crystalline precipitates are collected by filtration, and washed with acetone. 9 g of isobutyrylmethylamine hydrochloride are obtained. Yield: 78.3%.
M.p. 154°–155° C.
IR $\nu_{max}^{Nujol}$ (cm$^{-1}$): 1722, 1686, 1644, 1590.

(4) 4.5 g of 4-chlorobenzoyl chloride are added dropwise to a mixture of 4 g of isobutyrylmethylamine hydrochloride, 9.8 g of sodium bicarbonate, 200 ml of ethyl acetate and 100 ml of water at 5° C. to 10° C. under stirring. The mixture is further stirred at room temperature for 3 hours. The ethyl acetate layer is collected, and said layer is washed with water, dried and then condensed under reduced pressure to remove solvent. 6.1 g of N-(4-chlorobenzoyl)isobutyrylmethylamine are obtained. Yield: 87.5%.

M.p. 118°–119° C.

IR $\nu_{max}^{Nujol}$ (cm$^{-1}$): 3330, 3100, 1720, 1640.

(5) 6 g of N-(4-chlorobenzoyl)isobutyrylmethylamine are dissolved in 30 ml of dimethylformamide, and 1.4 g of 61% sodium hydride are added thereto at −50° C. to −40° C. under stirring. When, 6.0 g of ethyl bromoacetate are added to the mixture at the same temperature. After the temperature of the mixture is risen to about 0° C. gradually, said mixture is further stirred until it becomes a clear solution. After the reaction, the mixture is neutralized with acetic acid, and then water is added thereto. The aqueous solution is extracted with ethyl acetate. The extract is washed with water, dried and then condensed under reduced pressure to remove solvent. The residue is recrystallized from a mixture of isopropyl ether and n-hexane. 7.5 g of ethyl 3-(4-chlorobenzoylamino)-3-isobutyrylpropionate are obtained. Yield: 92.0%.

M.p. 42°–44° C.

IR $\nu_{max}^{KBr}$ (cm$^{-1}$): 3330, 1720, 1640.

Preparation 2

(1) 4.5 g of isobutyrylmethylamine hydrochloride, 11 g of sodium bicarbonate and 4.81 g of benzoyl chloride are treated in the same manner as described in Preparation 1-(4). 6.07 g of N-benzoylisobutyrylmethylamine are thereby obtained. Yield: 90.5%.

M.p. 78°–80° C.

IR $\nu_{max}^{Nujol}$ (cm$^{-1}$): 3330, 1708, 1640.

(2) 6.8 g of N-benzoylisobutyrylmethylamine, 1.56 g of 61% sodium hydride and 6.1 g of ethyl bromoacetate are treated in the same manner as described in Preparation 1-(5). 6.54 g of ethyl 3-benzoylamino-3-isobutyrylpropionate are thereby obtained. Yield: 67.7%.

M.p. 44°–46° C.

IR $\nu_{max}^{KBr}$ (cm$^{-1}$): 3270, 1720, 1640.

Preparation 3

(1) 4.0 g of isobutyrylmethylamine hydrochloride, 6.1 g of sodium bicarbonate and 5.1 g of 4-fluorobenzoyl chloride are treated in the same manner as described in Preparation 1-(4). 5.8 g of N-(4-fluorobenzoyl)isobutyrylmethylamine are thereby obtained. Yield: 89.2%.

M.p. 107°–108° C.

IR $\nu_{max}^{Nujol}$ (cm$^{-1}$): 3350, 1715, 1640, 1600.

(2) 5.6 g of N-(4-fluorobenzoyl)isobutyrylmethylamine, 1.2 g of 61% sodium hydride and 4.61 g of ethyl bromoacetate are treated in the same manner as described in Preparation 1-(5). 7.0 g of ethyl 3-(4-fluorobenzoylamino)-3-isobutyrylpropionate are thereby obtained as oil. Yield: 90.0%

IR $\nu_{max}^{film}$ (cm$^{-1}$): 3330, 1720.

Preparation 4

(1) 3.8 g of isovalerylmethylamine hydrochloride, 5.04 g of sodium bicarbonate and 4.9 g of 4-chlorobenzoyl chloride are treated in the same manner as described in Preparation 1-(4). 6.2 g of N-(4-chlorobenzoyl)isovalerylmethylamine are thereby obtained. Yield: 98.0.

M.p. 127°–129° C.

IR $\nu_{max}^{Nujol}$ (cm$^{-1}$): 3330, 1718, 1635, 1600.

(2) 2.5 g of N-(4-chlorobenzoyl)isovalerylmethylamine, 0.5 g of 61% sodium hydride and 1.81 g of ethyl bromoacetate are treated in the same manner as described in Preparation 1-(5). 2.5 g of ethyl 3-(4-chlorobenzoylamino)-3-isovalerylpropionate are thereby obtained. Yield: 74.4%.

M.p. 61°–63° C. (decomp.).

IR $\nu_{max}^{Nujol}$ (cm$^{-1}$): 3290, 3050, 1780, 1725.

Preparation 5

(1) 2.75 g of isovalerylmethylamine hydrochloride, 3.8 g of sodium bicarbonate and 3.16 g of 4-fluorobenzoyl chloride are treated in the same manner as described in Preparation 1-(4). 4.0 g of N-(4-fluorobenzoyl)isovalerylmethylamine are thereby obtained. Yield: 82.9%.

M.p. 104°–105° C.

IR $\nu_{max}^{Nujol}$ (cm$^{-1}$): 3300, 3090, 1720, 1639.

(2) 4.0 g of N-(4-fluorobenzoyl)isovalerylmethylamine are dissolved in 20 ml of dimethylsulfoxide and 1.3 g of potassium hydroxide are added thereto at 5° C. to 10° C. under vigorous stirring. The mixture is further stirred for 10 minutes. 3.1 g of ethyl bromoacetate are added dropwise to the mixture at the same temperature, and said mixture is further stirred for 2 hours. After the reaction, the mixture is treated in the same manner as described in Preparation 1-(5). 3.5 g of ethyl 3-(4-fluorobenzoylamino)-3-isovalerylpropionate are thereby obtained as oil. Yield: 64.8%.

IR $\nu_{max}^{Nujol}$ (cm$^{-1}$): 3310, 1720, 1630.

Preparation 6

6.0 g of N-(4-chlorobenzoyl)acetylmethylamine, 2.0 g of potassium hydroxide and 5.8 g of ethyl bromoacetate are treated in the same manner as described in Preparation 5-(2). 5.0 g of ethyl 3-(4-chlorobenzoylamino)-3-acetylpropionate are thereby obtained. Yield: 59.2%.

M.p. 57°–59° C.

IR $\nu_{max}^{Nujol}$ (cm$^{-1}$): 3300, 1720, 1630.

Preparation 7

(1) 50.1 g of potassium t-butoxide are dissolved in 500 ml of tetrahydrofuran, and 37.0 g of methyl α-isocyanoacetate are added dropwise thereto at −50° C. to −40° C. The mixture is stirred at the same temperature for 30 minutes. 50.0 g of n-caproyl chloride are gradually added to the mixture at −50° C. to −40° C., and the mixture is stirred at the temperature below −30° C. for 20 hours. After the reaction, the mixture is treated in the same manner as described in Preparation 1-(1). 40 g of 5-n-pentyl-4-methoxycarbonyloxazole are thereby obtained as oil. Yield: 54.3%.

IR $\nu_{max}^{film}$ (cm$^{-1}$): 3140, 1770, 1740, 1610.

(2) 40 g of 5-n-pentyl-4-methoxycarbonyloxazole, 27 g of potassium hydroxide, 1000 ml of methanol and 50 ml of water are treated in the same manner as described in Preparation 1-(2). 29.7 g of 5-n-pentyl-4-oxazolecarboxylic acid are thereby obtained. Yield: 80%.

M.p. 84°–85° C.

IR $\nu_{max}^{Nujol}$ (cm$^{-1}$): 3120, 1690, 1610.

(3) 35.0 g of 5-n-pentyl-4-oxazolecarboxylic acid and 70 ml of 4N hydrochloric acid are treated in the same manner as described in Preparation 1-(3). 24.0 g of n-caproylmethylamine hydrochloride are thereby obtained. Yield: 75.9%.

M.p. 168°–170° C.

IR $\nu_{max}^{Nujol}$ (cm$^{-1}$): 1720, 1590.

(4) 15 g of n-caproylmethylamine hydrochloride, 19 g of sodium bicarbonate and 15.9 g of 4-chlorobenzoyl chloride are treated in the same manner as described in Preparation 1-(4). 17.0 g of N-(4-chlorobenzoyl)-n-caproylmethylamine are thereby obtained. Yield: 70%.

M.p. 120°–121° C.

IR $\nu_{max}^{Nujol}$ (cm$^{-1}$): 3300, 1730, 1715, 1640.

(5) 7.0 g of N-(4-chlorobenzoyl)-n-caproylmethylamine, 1.2 g of 61% sodium hydride and 4.38 g of ethyl bromoacetate are treated in the same manner as described in Preparation 1-(5). 5.2 g of ethyl 3-(4-chlorobenzoylamino)-3-n-caproylpropionate are thereby obtained. Yield: 56.2%.

M.p. 67°–69° C.

IR $\nu_{max}^{KBr}$ (cm$^{-1}$): 3300, 1720, 1635.

What we claim is:

1. A method for the treatment or prophylaxis of hyperlipidemia which comprises administering to a host a compound of the formula:

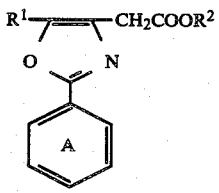

wherein Ring A is monohalogenophenyl, $R^1$ is an alkyl of one to 5 carbon atoms and $R^2$ is hydrogen or an alkyl of one to 2 carbon atoms.

2. A method for the treatment or prophylaxis of hyperlipidemia which comprises administering to a host an effective amount of a compound selected from the group consisting of ethyl 2-[2-(4-chlorophenyl)-5-isopropyl-4-oxazolyl]acetate, ethyl 2-[2-(4-fluorophenyl)-5-isopropyl-4-oxazolyl]acetate, 2-[2-(4-fluorophenyl)-5-isopropyl-4-oxazolyl]acetic acid and 2-[2-(4-chlorophenyl)-5-n-pentyl-4-oxazolyl]acetic acid, or a pharmaceutically acceptable salt thereof.

3. A method for the treatment or prophylaxis of hyperlipidemia which comprises administering to a host an effective amount of a compound of the formula:

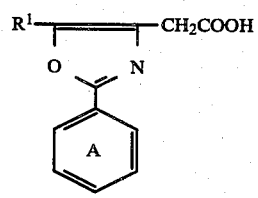

wherein Ring A is monohalogenophenyl, $R^1$ is an alkyl of one to 5 carbon atoms, or a pharmaceutically acceptable salt thereof.

* * * * *